United States Patent
Schuy et al.

(10) Patent No.: US 10,011,906 B2
(45) Date of Patent: Jul. 3, 2018

(54) METHOD FOR COATING A SURFACE OF A COMPONENT

(75) Inventors: Steffen Schuy, Mainz (DE); Martin Meisenheimer, Appenheim (DE); Florian Witte, Schwabenheim (DE)

(73) Assignee: Beohringer Ingelheim International GmbH, Ingelheim am Rhein ( * ) Notice: Subject to any disclaimer, the term of this patent is extended or adjusted under 35 U.S.C. 154(b) by 824 days.

(21) Appl. No.: 13/257,042

(22) PCT Filed: Mar. 22, 2010

(86) PCT No.: PCT/EP2010/053668
§ 371 (c)(1),
(2), (4) Date: Nov. 7, 2011

(87) PCT Pub. No.: WO2010/112358
PCT Pub. Date: Oct. 7, 2010

(65) Prior Publication Data
US 2012/0138713 A1   Jun. 7, 2012

(30) Foreign Application Priority Data

Mar. 31, 2009   (EP) .................................... 09156940

(51) Int. Cl.
*B05D 3/10*   (2006.01)
*C23C 18/12*   (2006.01)
(Continued)

(52) U.S. Cl.
CPC ........... *C23C 18/122* (2013.01); *A61M 11/00* (2013.01); *A61M 11/007* (2014.02);
(Continued)

(58) Field of Classification Search
USPC ........................................................ 427/600
See application file for complete search history.

(56) References Cited

U.S. PATENT DOCUMENTS 1,828,864 A   10/1931   Hopkins
2,015,970 A   10/1935   Schoene
(Continued)

FOREIGN PATENT DOCUMENTS

AU   2005201364 A1   7/2006
CA   1094549 A   1/1981
(Continued)

OTHER PUBLICATIONS

Cras et al "Comparison of chemical cleaning methods of glass in preparation for silanization" Biosensors & Bioelectronics 14 (1999) 683-688.*
(Continued)

*Primary Examiner* — Nathan H Empie
(74) *Attorney, Agent, or Firm* — Marc Began; Philip I. Datlow

(57) ABSTRACT

The invention relates to a method for coating a surface (44), in particular a microstructured surface, of a component (55) comprising different materials, in particular glass and silicon, wherein the surface (44) is first activated and then coated, wherein an oxidising solution, a basic solution or an acid-oxidising solution is used to activate the surface (44).

17 Claims, 2 Drawing Sheets

Figure 1:
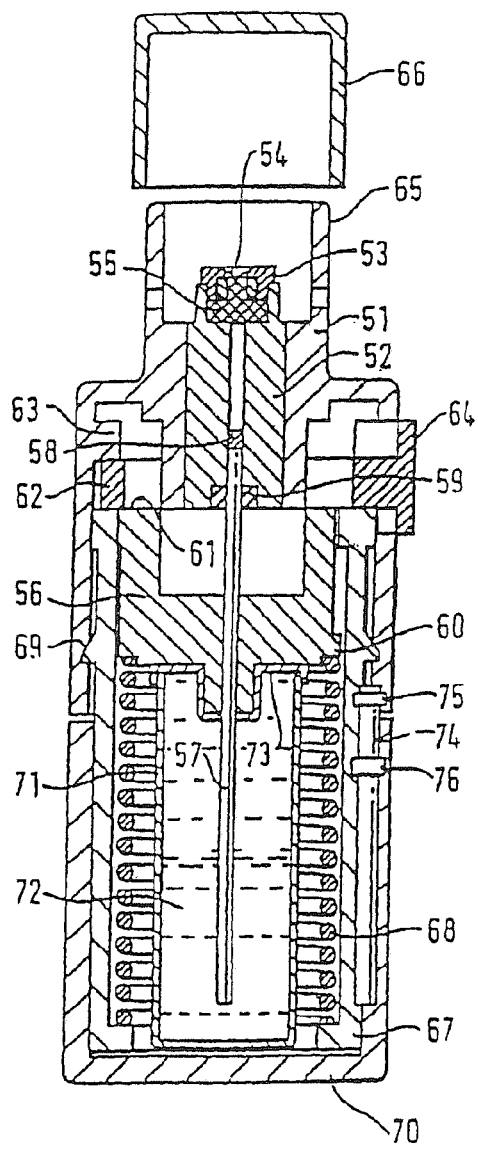
Figure 2:
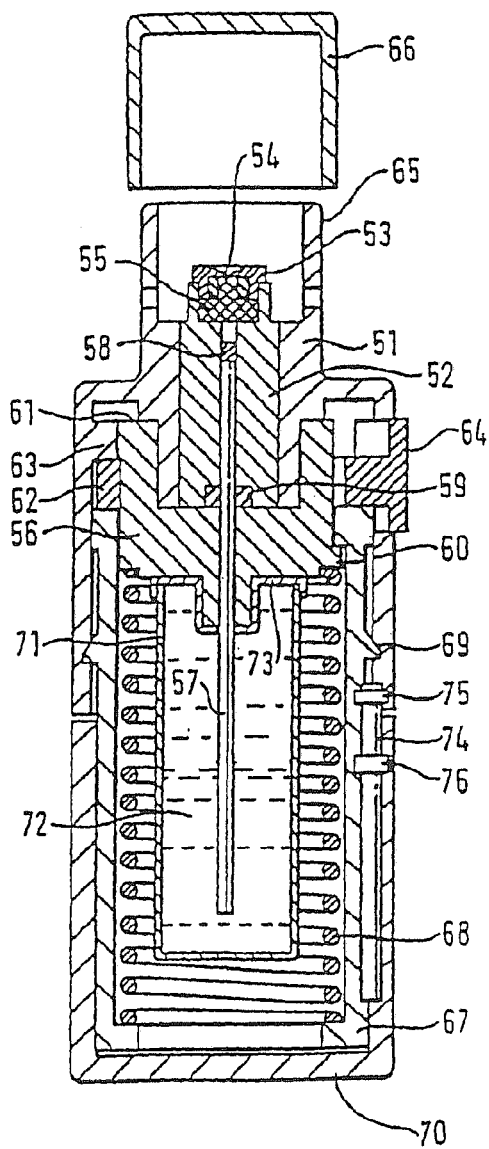
Figure 3:
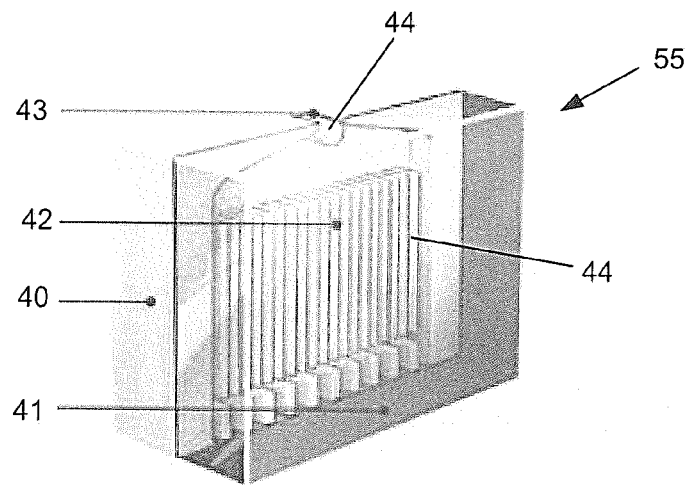
Figure 4:
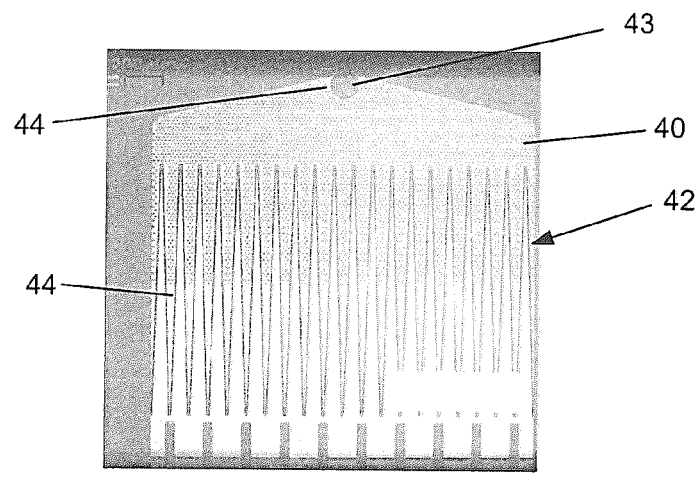
Figure 5:
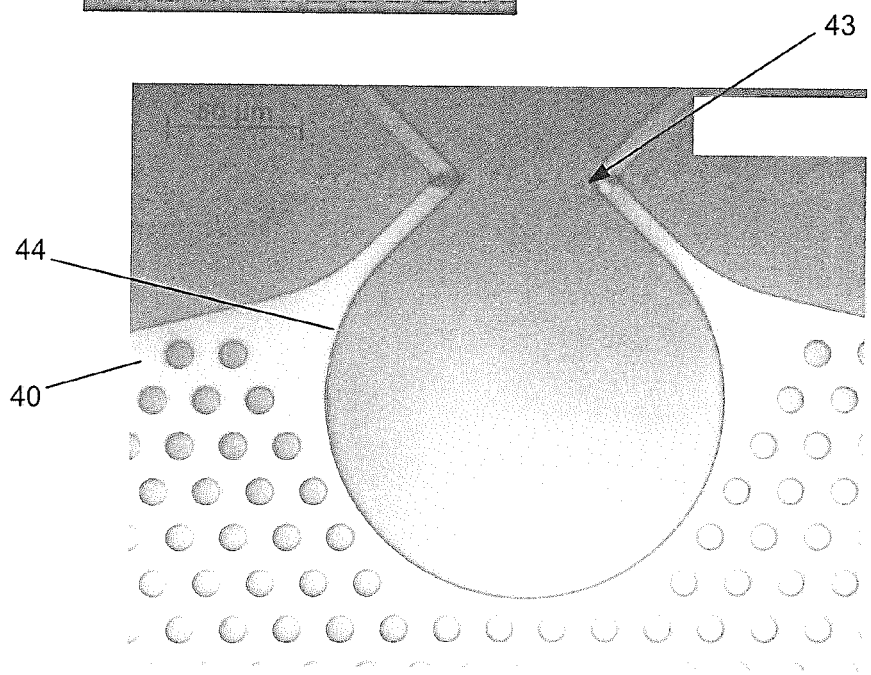

(51) Int. Cl.
*A61M 11/00* (2006.01)
*A61M 15/00* (2006.01)
*B05B 11/00* (2006.01)
*A61M 11/06* (2006.01)

(52) U.S. Cl.
CPC ..... *A61M 15/0065* (2013.01); *B05B 11/3001* (2013.01); *B05B 11/308* (2013.01); *B05B 11/3067* (2013.01); *B05B 11/3091* (2013.01); *C23C 18/1295* (2013.01); *A61M 11/06* (2013.01); *A61M 15/0071* (2014.02); *A61M 2205/0222* (2013.01); *A61M 2205/0244* (2013.01); *B05B 11/0043* (2013.01); *B05B 11/309* (2013.01)

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,120,995 A | 10/1978 | Phipps et al. |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A * | 9/1989 | Dreinhoff ................. 347/68 |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,973,318 A | 11/1990 | Holm et al. |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A * | 10/1992 | Marks et al. ................. 428/447 |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,584,285 A | 12/1996 | Salter et al. |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |

(56) References Cited

U.S. PATENT DOCUMENTS

| | | |
|---|---|---|
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,871,010 A * | 2/1999 | Datta ............ A61M 15/0045 128/203.12 |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,777 A | 3/2000 | Faithfull et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,109,479 A | 8/2000 | Ruckdeschel |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,336,453 B1 | 1/2002 | Scarrott et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 * | 5/2002 | Yan et al. ............... 427/169 |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |

(56) References Cited

U.S. PATENT DOCUMENTS

| | | |
|---|---|---|
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,167,171 B2 | 5/2012 | Moretti |
| 8,298,622 B2 | 10/2012 | Nakayama et al. |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 | 2/2015 | Holakovsky et al. |
| 8,960,188 B2 | 2/2015 | Bach et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0007155 A1 | 1/2002 | Freund et al. |
| 2002/0046751 A1 | 4/2002 | MacRae et al. |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0183225 A1 | 10/2003 | Knudsen |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0196660 A1 | 10/2003 | Haveri |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1* | 4/2004 | Sirejacob .................. 106/287.1 |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0164186 A1 | 8/2004 | Kladders et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0210199 A1 | 10/2004 | Atterbury et al. |
| 2004/0231667 A1 | 11/2004 | Horton et al. |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239886 A1 | 10/2006 | Nakayama et al. |
| 2006/0239930 A1 | 10/2006 | Lamche et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0264437 A1 | 11/2007 | Zimmermann et al. |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0060640 A1 | 3/2008 | Waldner et al. |
| 2008/0083408 A1 | 4/2008 | Hodson et al. |
| 2008/0092885 A1 | 4/2008 | von Schuckmann |
| 2008/0156321 A1 | 7/2008 | Bowman et al. |
| 2008/0197045 A1 | 8/2008 | Metzger et al. |
| 2008/0249459 A1 | 10/2008 | Godfrey et al. |
| 2008/0265198 A1 | 10/2008 | Warby |
| 2008/0283553 A1 | 11/2008 | Cox et al. |
| 2008/0299049 A1 | 12/2008 | Stangl |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0211576 A1 | 8/2009 | Lehtonen et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |

(56) References Cited

U.S. PATENT DOCUMENTS

| | | |
|---|---|---|
| 2009/0317337 A1 | 12/2009 | Schmidt |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2010/0258119 A1* | 10/2010 | Dams ............. A61M 15/009 128/203.15 |
| 2010/0313884 A1 | 12/2010 | Elliman |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0245780 A1 | 10/2011 | Helmer et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0811430 A1 | 3/1997 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |

(56) References Cited

FOREIGN PATENT DOCUMENTS

| | | |
|---|---|---|
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2002235940 A | 8/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 198100674 A1 | 3/1981 |
| WO | 198200785 A1 | 3/1982 |
| WO | 198300288 A1 | 2/1983 |
| WO | 198303054 A1 | 9/1983 |
| WO | 198605419 A1 | 9/1986 |
| WO | 198706137 A1 | 10/1987 |
| WO | 198803419 A1 | 5/1988 |
| WO | 198900889 A1 | 2/1989 |
| WO | 198900947 A1 | 2/1989 |
| WO | 198902279 A1 | 3/1989 |
| WO | 198903672 A1 | 5/1989 |
| WO | 198903673 A1 | 5/1989 |
| WO | 198905139 A1 | 6/1989 |
| WO | 199009780 A1 | 9/1990 |
| WO | 199009781 A1 | 9/1990 |
| WO | 1991014468 A1 | 10/1991 |
| WO | 199206704 A1 | 4/1992 |
| WO | 199217231 A1 | 10/1992 |
| WO | 199221332 A1 | 12/1992 |
| WO | 199222286 | 12/1992 |
| WO | 1993013737 A1 | 7/1993 |
| WO | 199325321 A1 | 12/1993 |
| WO | 1993024164 A1 | 12/1993 |
| WO | 9407607 A1 | 4/1994 |
| WO | 199417822 A1 | 8/1994 |
| WO | 199425371 A1 | 11/1994 |
| WO | 199427653 A2 | 12/1994 |
| WO | 199503034 A1 | 2/1995 |
| WO | 1995032015 A1 | 11/1995 |
| WO | 199600050 A1 | 1/1996 |
| WO | 1996006011 A2 | 2/1996 |
| WO | 199606581 A1 | 3/1996 |
| WO | 199623522 A1 | 8/1996 |
| WO | 199701329 A1 | 1/1997 |
| WO | 199706813 A1 | 2/1997 |
| WO | 199706842 A1 | 2/1997 |
| WO | 199712683 A1 | 4/1997 |
| WO | 1997012687 A1 | 4/1997 |
| WO | 199720590 A1 | 6/1997 |
| WO | 199723208 A1 | 7/1997 |
| WO | 199727804 A1 | 8/1997 |
| WO | 199735562 A1 | 10/1997 |
| WO | 199741833 A1 | 11/1997 |
| WO | 1998012511 A2 | 3/1998 |
| WO | 199827959 A2 | 7/1998 |
| WO | 199831346 A1 | 7/1998 |
| WO | 199839043 A1 | 9/1998 |
| WO | 1999001227 A1 | 1/1999 |
| WO | 1999007340 A1 | 2/1999 |
| WO | 1999011563 A1 | 3/1999 |
| WO | 1999016530 A1 | 4/1999 |
| WO | 1999043571 A1 | 9/1999 |
| WO | 199962495 A2 | 12/1999 |
| WO | 199965464 | 12/1999 |
| WO | 200001612 A2 | 1/2000 |
| WO | 200023037 A1 | 4/2000 |
| WO | 2000023065 A2 | 4/2000 |
| WO | 200027543 A1 | 5/2000 |
| WO | 200037336 A1 | 6/2000 |
| WO | 2000033965 A1 | 6/2000 |
| WO | 200049988 A2 | 8/2000 |
| WO | 200064779 A1 | 11/2000 |
| WO | 200113885 A1 | 3/2001 |
| WO | 200128489 A1 | 4/2001 |
| WO | 2001064182 A2 | 9/2001 |
| WO | 200187392 A1 | 11/2001 |
| WO | 2001085097 A2 | 11/2001 |
| WO | 200197888 A2 | 12/2001 |
| WO | 200198175 A1 | 12/2001 |
| WO | 200198176 A2 | 12/2001 |
| WO | 200204054 A1 | 1/2002 |
| WO | 200205879 A1 | 1/2002 |
| WO | WO 0216046 A1 * 2/2002 ............... B05B 5/00 |
| WO | 200217988 A2 | 3/2002 |
| WO | 200232899 A1 | 4/2002 |
| WO | 2002034411 A1 | 5/2002 |
| WO | 2002070141 A1 | 9/2002 |
| WO | 2002089887 A1 | 11/2002 |
| WO | 2003002045 A1 | 1/2003 |
| WO | 2003014832 A1 | 2/2003 |
| WO | 2003020253 A2 | 3/2003 |
| WO | 2003022332 A2 | 3/2003 |
| WO | 2003035030 A1 | 5/2003 |
| WO | 2003037159 A2 | 5/2003 |
| WO | 2003037259 A2 | 5/2003 |
| WO | 2003049786 A2 | 6/2003 |
| WO | 2003050031 A1 | 6/2003 |
| WO | 2003053350 A2 | 7/2003 |
| WO | 2003057593 A1 | 7/2003 |
| WO | 2003059547 A1 | 7/2003 |
| WO | 2003068299 A1 | 8/2003 |
| WO | 2003087097 A1 | 10/2003 |
| WO | 2003097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 200433954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2004098795 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007049239 A2 | 5/2007 |

(56) References Cited

FOREIGN PATENT DOCUMENTS

| | | | |
|---|---|---|---|
| WO | 2007060104 A2 | 5/2007 | |
| WO | 2007060105 A1 | 5/2007 | |
| WO | 2007060106 A1 | 5/2007 | |
| WO | 2007060107 A1 | 5/2007 | |
| WO | 2007060108 A2 | 5/2007 | |
| WO | 2007062721 A1 | 6/2007 | |
| WO | 2007090822 A2 | 8/2007 | |
| WO | 2007101557 A2 | 9/2007 | |
| WO | 2007128381 A1 | 11/2007 | |
| WO | 2007134965 A1 | 11/2007 | |
| WO | 2007134966 A1 | 11/2007 | |
| WO | 2007134967 A1 | 11/2007 | |
| WO | 2007134968 A1 | 11/2007 | |
| WO | 2007141201 A1 | 12/2007 | |
| WO | 2007141203 A1 | 12/2007 | |
| WO | 2008023017 A2 | 2/2008 | |
| WO | 2008047035 A2 | 4/2008 | |
| WO | 2008077623 A1 | 7/2008 | |
| WO | 2008124666 A2 | 10/2008 | |
| WO | 2008138936 A2 | 11/2008 | |
| WO | 2008146025 A2 | 12/2008 | |
| WO | 2009006137 A1 | 1/2009 | |
| WO | 2009047021 A1 | 4/2009 | |
| WO | 2009047173 A2 | 4/2009 | |
| WO | 2009050978 A1 | 4/2009 | |
| WO | 2009090245 A1 | 7/2009 | |
| WO | 2009103510 A1 | 8/2009 | |
| WO | 2009115200 A1 | 9/2009 | |
| WO | 2010005946 A2 | 1/2010 | |
| WO | 2010006870 A1 | 1/2010 | |
| WO | 2010094305 A1 | 8/2010 | |
| WO | 2010094413 A2 | 8/2010 | |
| WO | 2010112358 A2 | 10/2010 | |
| WO | 2010133294 A2 | 11/2010 | |
| WO | 2011006711 A1 | 1/2011 | |
| WO | 2011064160 A1 | 6/2011 | |
| WO | 2011064163 A1 | 6/2011 | |
| WO | 2011064164 A1 | 6/2011 | |
| WO | 2011131779 A1 | 10/2011 | |
| WO | 2011154295 A2 | 12/2011 | |
| WO | 2011160932 A1 | 12/2011 | |
| WO | 2012130757 A1 | 10/2012 | |
| WO | 2012159914 A1 | 11/2012 | |
| WO | 2012160047 A2 | 11/2012 | |
| WO | 2012160052 A1 | 11/2012 | |
| WO | 2012161685 A1 | 11/2012 | |
| WO | 2012162305 A1 | 11/2012 | |
| WO | 2013110601 A1 | 8/2013 | |
| WO | 2013152861 A1 | 10/2013 | |
| WO | 2013152894 A1 | 10/2013 | |
| WO | 2015018901 A1 | 2/2015 | |
| WO | 2015018903 A1 | 2/2015 | |
| WO | 2015018904 A1 | 2/2015 | |
| WO | 2015169431 A2 | 11/2015 | |
| WO | 2015169732 A1 | 11/2015 | |
| ZA | 199901520 A | 12/1999 | |

OTHER PUBLICATIONS

Hoffman et al "Mixed self-assembled monolayers (SAMs) consisting of mehyoxy-tri(ethylene glycol)-terminated and alkyl-terminated dimethylchlorosilanes control the non-specific adsorption of proteins at oxidic surfaces" J. of Colloid and Interface Science 295 (2006) 427-435.*
Husseini et al "Alkyl Monolayers on Silica Surfaces Prepared Using Neat, Heated Dimethylmonochlorosilanes with Low Vapor Pressures" Langmuir 2003, 19, 5169-5171.*
Elwenspoek et al, Mechanical Microsensors, Springer-Verlag Berlin Heidelberg (c) 2001 4 pages.*
Kutchoukov et al "Fabrication of nanofluidic devices using glass-to-glass anodic bonding" Sensors and Actuators A 114 (2004) p. 521-527.*
Mandel et al "Cytophobic surface modification of microfluidic arrays for in situ parallel peptide synthesis and cell adhesion assays" Biotechnol Prog. Author manuscript available in PMC Sep. 21, 2008 19 pgs.*
Wang et al "Self-Assembled Silane Monolayers: Fabrication with Nanoscale Uniformity"; Langmuir 2005, 21, 1848-1857.*
Ackermann et al.; Quantitative Online Detection of Low-Concentrated Drugs via a SERS Microfluidic System; ChemPhysChem; 2007; vol. 8; No. 18; pp. 2665-2670.
Wang et al.; Self-Assembled Silane Monolayers: Fabrication with Nanoscale Uniformity; Langmuir; 2005; vol. 21; No. 5; pp. 1848-1857.
Henkel et al.; Chip modules for generation and manipulation of fluid segments for micro serial flow processes; Chemical Engineering Journal; 2004; vol. 101; pp. 439-445.
Han et al.; Surface activation of thin silicon oxides by wet cleaning and silanization; Thin Solid Films; 2006; vol. 510; No. 1-2; pp. 175-180.
International Search Report, Form PCT/ISA/210, for corresponding PCT/EP2010/053668; dated Nov. 8, 2010.
"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of JPH07118164, 1995.
Abstract in English of JPH07118166, 1995.
Abstract in English of JPH08277226, 1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Bocci et al., "Pulmonary catabolism of interferons: alveolar absorption of 125I-labeled human interferon alpha is accompanied by partial loss of biological activity". Antiviral Research, vol. 4, 1984, pp. 211-220.
China Suppliers, Shanghai Lite Chemical Technology Co., Ltd. Product details on polyvinylpyrrolidones. Obtained online by the USPTO examiner on Apr. 24, 2011.
Diamond et al., "Substance P Fails to Mimic Vagally Mediated Nonadrenergic Bronchodilation". Peptides, vol. 3, 1982, pp. 27-29.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
Lougheed et al., "Insulin Aggregation in Artificial Delivery Systems". Diabetologia, vol. 19, 1980, pp. 1-9.
Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.

(56) References Cited

OTHER PUBLICATIONS

Abstract in English of JPH057246, 1993.
Abstract in English of JPH0553470, 1993.
Chen, F-K et al., "A study of forming pressure in the tube-hydroforming process". Journal of Materials Processing Technology, 192-193, 2007, p. 404-409.
Abstract in English of FR2604363, Sep. 30, 1986.
"Activate". Collins English Dictionary, London: Collins, 2000, 2 pages. [Retrieved at http://search.credoreference.com/content/entry/hcengdict/activate/0 on Jun. 12, 2014].
Beasley R et al: "Preservatives in Nebulizer solutions: Risks without Benefit" Pharmacotherapy, Boston, US, Bd. 18, Nr. 1, Jan. 1998, pp. 130-139.
Beasley R et al: "Preservatives in Nebulizer solutions: Risks without Benefit" Pharmacotherapy, Boston, US, Bd. 18, Nr. 1, Jan. 1998.
JP2005144459—English language abstract only.
Abstract in English for WO2009050978, 2009.
Abstract in English for JP2002-235940, 2001.
Myung-Suk Chun et al, "Fabrication and validation of a multi-channel type microfluidic chip for electronical streaming potential devices", Lab on a Chip: miniaturisation for chemistry, physics, biology, materials science and bioengineering, 2006, vol. 6, No. 2, pp. 302-309.

\* cited by examiner

METHOD FOR COATING A SURFACE OF A COMPONENT

The invention relates to a method for coating a surface, in particular a micro-structured surface, of a component comprising different materials, in particular glass and silicon, wherein the surface is first activated and then coated, a coated component and a nebuliser having a coated component.

WO 91/14468 A1 and WO 97/12687 A1 each show a nebuliser which is marketed in the form of an inhaler under the brand name "Respimat" by Boehringer Ingelheim Pharma GmbH & Co. KG. The nebuliser is used for propellant-free administration of a metered quantity of a liquid medicament for inhalation. In the inhaler, liquid medicament formulations are stored in a reservoir and conveyed through a riser tube into a metering chamber from which they are finally expelled through a nozzle.

The nozzle has a liquid inlet side and a liquid outlet side. On the liquid inlet side is an opening through which the liquid medicament coming from the metering chamber is able to enter the nozzle. On the opposite side, the free end face of the nozzle, the liquid then emerges through two nozzle openings which are aligned such that the jets of liquid emerging from the openings strike one another and are thereby nebulised. The nozzle openings are formed in at least two superimposed plates, at least one of which has a microstructure, so that the two plates firmly attached to one another define on one side a liquid inlet, adjoining which is a channel and/or filter system that opens into the nozzle openings. The two plates with the microstructure and the nozzle openings are referred to as a uniblock in the context of the Respimat technology.

A nebuliser of this kind usually delivers formulations based on water or water/ethanol mixtures and within a short time is able to nebulise a small amount of the liquid medicament formulation, in the therapeutically required dose, into an aerosol suitable for therapeutic inhalation. Using the nebuliser it is possible to nebulise quantities of less than 100 microliters in, for example, one actuation to form an aerosol with an average particle size of less than 20 microns, such that the inhalable part of the aerosol already corresponds to the therapeutically effective amount.

In the nebuliser with Respimat technology the medicament solution is converted by a high pressure of up to 300 bar into a slowly moving aerosol mist destined for the lungs, which can then be breathed in by the patient. In rare cases, during the use of the nebuliser, residues of the formulation solution may adhere to the nozzle outlets as a contaminant, accumulate thereon and lead to clogging of the nozzle outlets, which may be accompanied by a deflection of the jets of liquid and a change in the fine particle fraction. Even if this effect is very rare in a nebuliser of the Respimat technology, there is a need to avoid deposits for reasons of quality control.

To avoid contamination of an outer surface of the nozzle system or a mouthpiece by precipitated liquid with fine particle fractions, DE 103 00 983 A1 proposes that the corresponding surfaces should be at least partially micro- or nano-structured.

The aim of the invention is to provide a method and a component as well as a nebuliser comprising a component of the kind described hereinbefore which is of self-cleaning design with a thin functionalising coating.

According to the invention the objective is achieved by a method which uses an oxidising solution, a basic solution or an acid-oxidising solution to activate the surface.

Surprisingly, it has been found that the solutions mentioned above can be used to activate surfaces of two different materials, particularly silicon and glass, which are joined together to form a monolithic component. In the literature, a special solution is always assigned to a particular material in order to produce the reactive groups needed for interface functionalisation, as the activation has to be matched to the particular substrate and specifically developed for different materials. For example, the activation of the surface of the component is carried out using a so-called piranha solution, namely the powerfully oxidising peroxomonosulphuric acid (concentrated sulphuric acid: hydrogen peroxide solution (30%) in the ratio 7:3), at 70° C. for 20 minutes. Alternatively, RCA cleaning may be used which is normally used for wafer cleaning in microelectronics. This uses the following solution: water:ammonia solution (25%):hydrogen peroxide solution (30%), in the ratio 5:1:1. The component is exposed to the solution at 75° C. for 20 minutes.

Preferably, a cell cleaner is used as the basic solution for activating the surface. Preferably the cell or glass cleaner made by Hellma GmbH & Co. KG, of Müllheim, Germany, known under the brand name " Hellmanex solution" is used, as an aqueous 2% solution at 70° C. for 2×20 minutes in the ultrasound bath, although the manufacturer advises against the use of ultrasound in conjunction with their "Hellmanex solution". The Hellmanex solution ensures activation which is effective on all kinds of materials, particularly silicon and glass, in order to produce reactive interfaces.

Expediently, before being activated, the surface is cleaned, particularly with isopropanol and water. The component is immersed in isopropanol for five minutes and in water for five minutes. According to one feature, the surface is treated in a solution of hydrofluoric acid after cleaning. It is bathed for about 20 minutes in an aqueous 3% hydrofluoric acid solution (HF).

According to a further feature, functional silanes in non-polar, aprotic or polar-protic solvents are used to coat the surface. The coating is very thin and is provided as a monolayer. The component with its activated surfaces is immersed for about two hours, in a toluene reaction, in a 0.1 to 1% solution of functional trichlorosilanes or dimethylmonochlorosilanes in dry non-polar, aprotic solvents such as toluene, benzene, carbon tetrachloride, n-alkanes ($C_5$-$C_{10}$) or the like. Then the component is dried in a nitrogen current and heat-treated in an oven for about one hour at about 120° C. After the heat-treatment excess and non-covalently bound residues are washed off the component using toluene and isopropanol. When the reaction is alcoholic, particularly isopropanolic, first of all a reaction solution has to be activated in order to be able to carry out interface functionalisation of the component with its activated surfaces of silicon and glass. A 0.1 to 1% solution of functional triethoxysilanes in 2-propanol/water/hydrochloric acid (HCl) in a ratio of 90 to 98:2 to 10:0.2 to 0.5 is stirred for about five hours at ambient temperature. Then the component with its activated surfaces is immersed in the solution for about two hours. After the component has been taken out of the solution the excess solution is carefully removed from the component, for example by allowing it to drip onto an absorbent non-woven fabric. Then the component is kept at a controlled 120° C. for about two hours. Any excess and non-covalently bound residues are washed off the component using isopropanol and water after the heat treatment. The following categories of materials are used to coat the surfaces: perfluoroalkylsilanes, alkylsilanes, aminoalkylsilanes, carboxylic acid silanes, trimethylammonium silanes of different chain lengths, particularly $C_4$-$C_{18}$, while the functional silanes used may be reactive trihalosilanes ($R_1$—Si—$R_3$, where R=Cl, Br), monohalodimethylsilanes ($R_1$—Si(CH3)$_2$R, where R=Cl, Br) or trialkoxysilanes ($R_1$—Si—$R_3$, where R=methoxy or ethoxy groups).

To ensure satisfactory wetting of the surfaces of the component that are to be coated, in order to coat the surfaces the component is advantageously treated with ultrasound in the reaction solution. The ultrasound treatment in particular ensures the exchange of the reaction solution in the capillaries of the component.

The objective is achieved in the component comprising at least two plates firmly joined together, at least one of which has a microstructure to form a channel and/or filter system and at least one nozzle opening adjoining it, by the fact that at least the surface of the microstructure has a coating which has been applied by the method described above.

As a result of this, any interaction of components and particles of the formulation expelled through the nozzle opening with the interfaces of the component is prevented. The free energy of the surface and hence its wettability is minimised in this area, resulting in a reduction in the immobilisation of residues of material on the nozzle outlet, i.e. in the immediate vicinity of the nozzle opening. When the component is used, the residues of material are expelled from the component and the coated component is self-cleaning, thanks to the use of the monomolecular, covalently bound non-stick coating. The functionalisation can be altered variably, depending on the interaction of different ingredients of the formulation with the interfaces of the component and may, for example, have hydrophilic or hydrophobic, positively or negatively charged, oleophillic or oleophobic properties.

One plate expediently consists of silicon while the other plate is glass. The silicon plate is provided with a microstructure, i.e. it comprises the channel or filter system and the nozzle openings and is adhesively bonded to the plate made of glass.

The component consists of the two plates of glass and silicon firmly joined together, while the plate consisting of silicon has one or more microstructured channels which connect the inlet side to the outlet side. On the outlet side there may be at least one round or non-round nozzle opening 2-10 μm deep and 5-15 μm wide, the depth preferably being 4.5 to 6.5 μm and the length being 7 to 9 μm. In the case of a plurality of nozzle openings, preferably two, the directions of flow through the nozzles in the component which essentially forms a nozzle body extend parallel to one another or are inclined towards one another in the direction of the nozzle opening. In a component having at least two nozzle openings on the outlet side, the directions of flow may slope towards one another at an angle of 20° to 160°, preferably at 60° to 150°, more preferably 70° to 100°. The nozzle openings are preferably arranged at a distance of 10 to 200 μm, more preferably at a distance of 10 to 100 μm, particularly preferably 30 to 70 μm. A distance of 50 μm is most preferred. The directions of flow meet accordingly in the vicinity of the nozzle openings. In the interests of simplicity an embodiment will be described hereinafter in which only the silicon plate of the component has relief-like microstructures, but not the plate made of glass. In other embodiments the situation is exactly the reverse, or both plates comprise these microstructures. On the silicon plate, a set of channels may be formed on the flat surface in order to create a plurality of filter passages (filter channels) in co-operation with the substantially flat surface of the glass plate. Additionally, the silicon plate may have a plenum chamber the ceiling of which is in turn formed by the glass plate. The plenum chamber may be provided in front of or behind the filter channels. It is also possible to have two such plenum chambers. Another set of channels on the substantially flat surface of the silicon plate which is provided after the filter channels forms, together with the glass plate, a set of channels that provide a plurality of nozzle outlet passages. Preferably, the total cross-sectional area of the nozzle outlets is 25 to 500 $\mu m^2$. The entire cross-sectional area is preferably 30 to 200 $\mu m^2$. In another embodiment this nozzle construction also has only a single nozzle opening. In other embodiments of this kind the filter channels and/or the plenum chamber are omitted. Preferably, the filter channels are formed by projections arranged in a zig-zag configuration. Thus, for example, at least two rows of the projections form a zig-zag configuration of this kind. A number of rows of projections may also be formed, the projections being laterally offset from one another in order to form additional rows that are skewed in relation to these rows, these additional rows mentioned above then forming the zig-zag configuration. In such embodiments the inlet and outlet may each comprise a longitudinal slot for unfiltered or filtered fluid, each of the slots being substantially the same width as the filter and substantially the same height as the projections on the inlet and outlet sides of the filter. The cross-section of the passages formed by the projections may be perpendicular to the direction of flow of the fluid and may decrease from one row to the next, viewed in the direction of flow. Also, the projections that are arranged closer to the inlet side of the filter may be larger than the projections that are arranged closer to the outlet side of the filter. In addition, the spacing between the silicon plate and the glass plate may become narrower in the region from the inlet side to the outlet side. The zig-zag configuration which is formed by at least two rows of projections has an angle of inclination of preferably 20° to 250°. Further details of this construction of the component can be found in WO 94/07607.

Finally, the objective is achieved with a nebuliser for delivering a specific amount of a fluid, in particular a fluid containing a medicament, as an aerosol, using the component of the kind described hereinbefore.

It will be understood that the features mentioned above and those to be explained hereinafter may be used not only in the particular combinations stated but also in other combinations. The scope of the invention is defined only by the claims.

The invention is hereinafter described in more detail by means of an embodiment by way of example, by reference to the attached drawings, wherein:

FIG. 1 is a longitudinal section through a nebuliser according to the invention with a tensioned spring, FIG. 2 is a longitudinal section through the nebuliser according to FIG. 1 with the spring relaxed, FIG. 3 is a perspective view of a component according to the invention, FIG. 4 is a front view of the component according to FIG. 3 and FIG. 5 is a magnified partial representation of the component according to FIG. 3.

An upper housing part 51 of the nebuliser comprises a pump housing 52 on the end of which is mounted a holder 53 for a nebuliser nozzle. In the holder 53 is a recess 54 that widens outs and the component 55 in the form of a nozzle body. A hollow piston fixed in a power take-off flange 56 of a locking clamping mechanism projects partly into a cylinder of the pump housing 52. At its end the hollow piston 57 carries a valve body 58. The hollow piston 57 is sealed off by a gasket 59. Inside the upper housing part 51 is a stop 60 of the power take-off flange 56 on which a compression spring 68 rests. After the tensioning of the compression spring 68 a locking member 62 slides between a stop 61 on the power take-off flange 56 and a support 63 in the upper housing part 51. An actuating button 64 is connected to the locking member 62. The upper housing part 51 ends in a mouthpiece 65 and is closed off by a removable protective cap 66.

A spring housing 67 with the compression spring 68 is rotatably mounted on the upper housing part 51 by means of snap-fit lugs 69 and a rotary bearing. A lower housing part 70 is pushed over the spring housing 67 and inside the spring housing 67 is a storage container 71 for fluid 72 which is to be nebulised. The storage container 71 is closed off by a stopper 73 through which the hollow piston 57 projects into the storage container 71 and dips its end into the fluid 72, i.e. the supply of active substance solution.

A spindle 74 for a mechanical counter (optional) is provided in an outer surface of the spring housing 67. A drive pinion 75 is located at the end of the spindle 74 facing the upper housing part 51. On the spindle 74 is a slider 76.

The component 55—a so-called uniblock—comprises two plates 40, 41 firmly joined together, of which one plate 40 is made of silicon and has a microstructure 42 for forming a channel or filter system and an adjacent nozzle opening 43. The silicon plate 40 is firmly attached to the glass plate 41 on the side having the microstructure 42.

At least the surface 44 of the microstructure 42 has a coating consisting of functional silanes which prevents any interaction of ingredients and particles of the formulation expelled through the nozzle opening 43 with the interfaces of the component 55. During the use of the nebuliser comprising the component 55, the material residues are expelled from the component 55 and the coated component 55 is self-cleaning thanks to the use of the monomolecular, covalently bound non-stick coating.

The surfaces 44 of the component 55, particularly the microstructure 42, are first cleaned by dipping the component 5 first into isopropanol for five minutes and then into water for five minutes. Then the component 55 is bathed for about 20 minutes in an aqueous 3% hydrofluoric acid solution (HF).

The activation of the surface 44 itself is carried out using a cell cleaner, particularly the cell or glass cleaner known by the brand name "Hellmanex solution" and produced by Hellma GmbH & Co. KG, of Müllheim, Germany, as an aqueous 2% solution, at 70° C. for 2×20 minutes in an ultrasound bath.

For functionalisation, 1H,1H,2H,2H-perfluorooctyltriethoxysilane is used, for example, which is marketed for example under the brand name Dynasylan by Evonik AG of Düsseldorf. After the component 55 has been exposed for about two hours to a solution containing the functional silane under the effect of ultrasound, the excess solution is allowed to drip off the component 55 and the component is treated for about one to two hours at 120° C. in an oven. After the heat treatment any excess and non-covalently bound residues are washed off the component 55 using isopropanol and water.

The invention claimed is:

1. A method for preparing a nebulizer, the method comprising: coating a microstructured surface within a component comprising glass and silicon, wherein the component consists of a plate of glass and a plate of silicon firmly joined together and at least one of the plates has one or more microstructured channels, wherein the surface is first activated and then coated, characterized in that:
an oxidizing solution, a basic solution or an acid-oxidizing solution is used to activate the surface,
before the activation the surface is cleaned, and
coating the surface comprises:
applying a reaction solution to coat the microstructured channels, the reaction solution comprising functional silanes in non-polar, aprotic or polar-protic solvents, and
treating the microstructured surface with ultrasound during application of the reaction solution, wherein the ultrasound treatment causes flow of the reaction solution into the microstructured channels; and
incorporating the component into a medical device configured to nebulize a liquid medicament passed through the one or more microstructured channels.

2. The method according to claim 1, characterized in that the coated component is washed.

3. The method according to claim 1, wherein the oxidizing solution which is used for activating the surface is a solution consisting of water, ammonia solution, containing 25% ammonia, and hydrogen peroxide solution, containing 30% hydrogen peroxide, in the ratio 5:1:1.

4. The method according to claim 1, wherein a piranha solution is used as an acid-oxidizing solution for activating the surface.

5. The method according to claim 1, wherein before the activation the surface is cleaned using isopropanol and water.

6. The method according to claim 1, wherein for coating the surface, perfluoroalkylsilanes or alkylsilanes are used.

7. The method according to claim 6, wherein for coating the surface perfluoroalkl silanes or trialkoxysilanes are used.

8. The method according to claim 1, wherein for coating the surface, trihalosilanes, monohalodimethylsilanes or trialkoxysilanes are used.

9. The method according to claim 8, wherein dimethylmonochlorosilanes in dry non-polar, aprotic solvents are used for coating.

10. The method according to claim 9, wherein for coating the component is immersed in a solution of dimethylmonochlorosilanes and then dried in a nitrogen current.

11. The method according to claim 8, wherein a solution of trialkoxysilanes is used for coating.

12. The method according to claim 11, wherein a 0.1 to 1% solution of functional triethoxysilanes in 2-ropanol/water/hydrochloric acid is stirred for about five hours and the component with its activated surfaces is then immersed in the solution.

13. The method according to claim 11, wherein after the component has been taken out of the solution, the excess solution is removed from the component by allowing it to drip.

14. The method according to claim 11, wherein the trialkoxysilanes used are trimethoxysilanes or triethoxysilanes.

15. The method according to claim 1, wherein after the coating the component is heat-treated.

16. The method according to claim 15, wherein after the coating the component is heat-treated for 1 to 2 hours at 120° C.

17. The method according to claim 1, wherein the reaction solution forms a coating layer on the one or more microstructured channels, and wherein the coating layer inhibits accumulation of a liquid medicament within the one or more microstructured channels.

* * * * *